United States Patent

Kiesele et al.

Patent Number: 5,281,324
Date of Patent: Jan. 25, 1994

[54] MEASURING SENSOR FOR DETECTING GASEOUS COMPONENTS

[75] Inventors: Herbert Kiesele, Lübeck; Jürgen Sohege, Stockelsdorf, both of Fed. Rep. of Germany

[73] Assignee: Drägerwerk Aktiengesellschaft, Lübeck, Fed. Rep. of Germany

[21] Appl. No.: 42,664

[22] Filed: Apr. 5, 1993

Related U.S. Application Data

[63] Continuation-in-part of Ser. No. 711,802, Jun. 7, 1991, Pat. No. 5,202,011.

[30] Foreign Application Priority Data

Jun. 9, 1990 [DE] Fed. Rep. of Germany ....... 4018597

[51] Int. Cl.$^5$ .......................................... G01N 27/26
[52] U.S. Cl. .................... 204/415; 204/412; 204/431; 204/432
[58] Field of Search ............... 204/412, 415, 431, 432

[56] References Cited

U.S. PATENT DOCUMENTS

| | | | |
|---|---|---|---|
| 3,505,196 | 1/1966 | Dahms | 204/409 |
| 3,767,552 | 10/1973 | Lauer | 204/415 |
| 3,988,233 | 10/1976 | Gamer et al. | 204/415 |
| 4,259,165 | 3/1981 | Miyake | 204/415 |
| 4,599,157 | 7/1986 | Suzuki et al. | 204/415 |
| 4,650,547 | 3/1987 | Gough | 204/153.17 |
| 4,997,541 | 3/1991 | Kiesele et al. | 204/415 |
| 5,092,980 | 3/1992 | Maurer et al. | 204/415 |
| 5,126,035 | 6/1992 | Kiesele et al. | 204/415 |

OTHER PUBLICATIONS

"Römpps Chemie-Lexikon" by Dr. Otto-Albrecht Neumüller, 7th Edition, 1974, p. 2515.

Primary Examiner—John Niebling
Assistant Examiner—Bruce F. Bell
Attorney, Agent, or Firm—Walter Ottesen

[57] ABSTRACT

The invention is directed to a measuring sensor for detecting gaseous components which operates in the diffusion limit current region. The measuring sensor includes a support body and has an electrolyte chamber partitioned by a diffusion membrane from the ambient containing the gaseous components. The measuring electrode of the measuring sensor is improved so that a simpler manipulation for covering the electrolyte chamber with a membrane is possible without endangering the mechanical stability of the membrane. During operation, the detection operation is intended to take place completely at that electrode surface which is in direct electrochemical exchange communication with the electrolyte supply. For this purpose, the coating is configured as an adherent layer to the support body so that it forms an impermeable adherence region in the lateral direction between coating and support body. A process for producing the measuring electrode is characterized in that the coating is adheringly applied to a front face of the support body which forms a closed surface. Thereafter, a membrane layer is applied to the coating and a break through for communicating with the electrolyte chamber is formed in the support body by removing a portion of the support body starting from a rear face thereof lying opposite the front face. The break through is formed by removing the portion of the support body through to the coating. In the completed measuring sensor, this permits the electrolyte from the electrolyte chamber to penetrate through the break through to the coating.

16 Claims, 2 Drawing Sheets

MEASURING SENSOR FOR DETECTING GASEOUS COMPONENTS

RELATED APPLICATION

This is a continuation-in-part of application Ser. No. 07/711,802, filed on Jun. 7, 1991, U.S. Pat. No. 5,202,011 and entitled "Measuring Sensor for Detecting Gaseous Components".

FIELD OF THE INVENTION

The invention relates to a measuring sensor for detecting gaseous components with the aid of an electrochemical measuring cell. The measuring cell includes a measuring electrode and a counter electrode disposed in an electrolyte with the electrolyte chamber being partitioned by a membrane from the ambient containing the components to be detected with the membrane being impermeable for the electrolyte but permeable for the components to be detected. The membrane has a surface facing toward the electrolyte on which a permeable electrically-conductive coating is provided. The membrane with the coating is applied to a supporting body which has at least one break through filled with the electrolyte and through which the electrolyte can penetrate up to the coating. The coating is joined to an electric signal terminal for forming a measuring electrode.

The invention also relates to a method for producing a measuring electrode structure for a measuring sensor of the kind described above.

BACKGROUND OF THE INVENTION

Measuring sensors of the kind described above are known from U.S. Pat. No. 3,767,552. The measuring characteristics of these measuring sensors are essentially determined in that the diffusion membrane remains in close proximity to the metallic supporting body configured as an electrode and from which the measuring signals are transmitted to an evaluation unit. For this purpose, complex clamping and sealing measures are necessary whereby the membrane applied to the supporting body is clamped thereover. In addition, an adequate seal of the electrolyte chamber with respect to the remainder of the measuring sensor housing must be provided for the assembled condition. In this connection, it is noted that the membrane cannot be expanded too greatly during the clamping process so that its diffusion characteristics for the gas component to be detected is not changed in an unwanted manner or that capillary-like expansion fissures are formed from which the electrolyte can escape unnoticed during storage or operation. Measuring sensors of the above kind operate in the so-called diffusion limited current region. For this reason, the signal quality is essentially dependent upon the following: the diffusion characteristic of the membrane for the gas component to be detected, the electrode structure and the coaction of the membrane and measuring electrode. It is desirable to select the diffusion membrane as a diffusion barrier which is as thin as possible and made of a material having a good diffusion constant in order that the shortest possible response time for the measuring sensor can be achieved when there is a change in the gas concentration. The handling of such an extremely thin membrane is especially difficult and the sealing measures are most complex especially during installation of the membrane.

A further disadvantageous influence on the measuring signal is caused by the condition that the membrane applied to the support body forms regions between the membrane and the support body wherein electrolyte liquid enters when the membrane is clamped in place. The electrolyte liquid takes up the reaction product from the conversion of the gas component to be detected, but a subsequent removal of this reaction product and a replacement with fresh electrolyte liquid is impeded. This leads to defective measurements as a consequence of the changing transport coefficients of the components in the electrolyte which participate in the reaction. In addition, electrolyte regions can form between the membrane and support body which participate in the gas exchange through the membrane but for which a long diffusion path in this electrolyte region is present for the reaction at the electrode. This leads to an increase of the response time and to a delayed adjustment of the stable final measurement value.

Special manipulation difficulties are associated with arrangements having membranes coated on one side with a conductive coating such as by means of a sputtering operation. This process does not lead to an especially good adherence capability between membrane and coating which becomes noticeable especially with the necessary introduction into the arrangement and impregnation with the electrolyte. Often, the coating separates from the membrane so that a close proximity of the coating to the membrane is no longer ensured. This increases the rejection of unsuitable gas-measuring cells in a production process which is already complex. Also, the manipulation of such sputtered membranes is quite problematical since stresses are generated in the membrane because of the sputtering and these stresses make an attachment free of folds difficult during further handling.

SUMMARY OF THE INVENTION

In view of the foregoing, it is an object of the invention to provide a measuring sensor of the kind described above which is so improved that a simpler handling for covering the electrolyte chamber with a membrane is provided without endangering its mechanical stability. During operation, the detection reaction takes place completely at that electrode surface which communicates directly with the electrolyte supply so as to permit an electrochemical exchange.

The measuring sensor of the invention is for detecting gaseous components in the ambient. The measuring sensor includes: a support body having an end face and defining a chamber; an electrolyte disposed in the chamber; a permeable, electrically-conductive coating on the end face; break through means extending from the chamber to the end face for permitting the electrolyte to penetrate to the coating; the coating being applied to the end face so as to form an adhering interface; a membrane separating the electrolyte from the ambient containing the gaseous components and being permeable to the gaseous components; the membrane being impermeable to the electrolyte in a lateral direction between the support body and the coating and being applied to the coating so as to form an adhering connection with the coating; an electrical signal lead connected to the coating so as to cause the coating to define a measuring electrode and have an electrochemically active surface at the interface; and, a counter electrode disposed in the electrolyte.

According to a feature of the invention, the coating is configured as an adherent layer to the support body and to the membrane and is configured so that it forms a region with respect to the electrolyte which is impermeable in the lateral direction between the coating and both the support body and the membrane.

The advantage of the invention is essentially seen in that the coating defines an adherence connection and thereby prevents the formation of any capillary intermediate spaces between the coating and both the support body and the membrane into which the electrolyte would penetrate. In this way, defective measurements as a consequence of long distance diffusion of the gaseous substance to be detected present in the electrolyte in a dissolved form and of the reaction products into the electrolyte after a completed reaction are avoided.

The coating defines the measuring electrode in the region of the break through. Metallized membranes have the following attributes: defined diffusion paths, no signal dependency on electrolyte layers between membrane and support body, and good coupling to the electrolyte reservoir. These attributes of the metallized membrane can be used because of the adherence connection between coating and membrane. In addition, a good stability as to form is ensured because of the adherence connection between the coating and support body and the handling is improved. If in addition, the support body is made of metal, it functions as an enlargement of the electrode wherein the gaseous substances to be detected can additionally be converted at the walls of the break through.

In this way, it is ensured that the electrochemical detection reaction takes place exclusively in the region of the electrolyte chamber surrounded by the coating and the support body. The membrane can now be applied directly to the coating with a suitable precipitation process and does not have to be placed on the support body for example via a clamping device whereby an expansion is prevented since the coating as an adherent layer provides a planar application of the membrane to the support body. Furthermore, a sealing of the membrane on the support body is unnecessary since a penetration of the electrolyte between the support body and the membrane from the electrolyte chamber is prevented. It is sufficient to seal the conveniently manipulable support body as a unit with the membrane applied. In this way, sealing measures between the membrane and the support body are unnecessary which would otherwise be inconvenient to effect and complex to handle.

A special advantage for the invention is further seen in that the electric contact of the electrode is very simple. If the support body is an electronic conductor, then the electrode leads can be placed on the body at any desired location. In the event that the support body is a non-conductor, end faces facing away from the break throughs provide adequate possibility to contact the coating through the membrane without influencing the function of the arrangement.

The method for making the electrode structure of the measuring sensor of the invention includes the steps of: applying a permeable, electrically-conductive coating to a closed front face of a support body so as to form an adhering interface therewith, the coating defining a measuring electrode having an electrochemically active surface at the interface; applying a membrane layer directly to the coating so as to form an adhering connection thereto, the membrane being permeable to the gaseous components and impermeable to the electrolyte; forming a break through in the support body by removing a portion thereof starting from a rear face of the support body and continuing to the front face thereby causing the break through to extend to the active surface, the rear face being opposite the front face; and, the break through being formed by removing the portion of the support body through to the coating so as to permit the electrolyte from the electrolyte chamber to penetrate through the break through to the coating and the electrochemically active surface thereof.

In the method for producing a measuring electrode structure, the selection of materials for the support body as well as for the coating to be applied and the membrane can be optimized in that the best possible adherence of the layers to each other and to the support body is obtained. In addition, the measuring electrode structure can be formed by suitable sequential coating processes. The application of the coating applied to the support body with the membrane on the coating permits the thinnest membrane thicknesses to be realized which leads to very short response times for the measuring operation. Typical layer thicknesses for the coating lie between 10 and 1,000 nanometers while the membrane typically has a thickness of between 0.5 to 15 micrometers. An application of a coated membrane to the support body is unnecessary which would be unreliable during handling and for obtaining a later successful measurement.

If the two layers are applied to the support body, then the support body can be thinned down at selected regions from its rear side by means of suitable processes with the structure being thinned in these regions to the extent that the coating applied to the front side is exposed. The membrane continues to adhere to the support body at those locations at which the coating has not been exposed so that at these locations, the membrane with the coating forms adhesion regions which are impermeable to the electrolyte. The break through required for access of the electrolyte to the coating of the membrane can thereby take place on a support body to which layers have been applied so that now a stable and manipulable measuring electrode structure has been obtained which is easily manipulable for a subsequent mechanical machining.

When using stronger support bodies, it is advantageous to partially complete the removal of material for the break through in the support body in advance of applying the coating by means of a first machining step so that a supporting layer with a closed surface remains for the application of the coating and the membrane layer. In this way, the bare support body can be structurally machined from its lower side so that the geometric location for the break through is predetermined but does not yet extend completely through the support body. In this way, the support body provided with a prestructured but yet incomplete break through is still in a condition wherein a closed coating and closed membrane layer can be applied to its front face. Thereafter, the break through can be completed up to the coating in a comparatively short-term machining step. This procedure is especially then advantageous if it is intended to prevent the applied coating and membrane layers to be affected by the completion of the break through. The removal of thicker layers provided with the coating can lead to stresses in the support body for non-uniform removal which can lead to damage of the membrane-coating configuration.

An especially advantageous configuration of the break through is seen in that a plurality of through channels are formed in the support body. These channels are partitioned one from the other by webs with the coating adhering to the respective end faces of the webs so that the electrolyte can penetrate in the channel space up to the coating but not penetrate between the coating and the end face of a web. The gas molecules to be detected can react completely within the channel space in that they are converted at the three phase boundary electrolyte/coating/membrane and their reaction products are completely removed and the consumed electrolyte can be renewed from the supply in the electrolyte chamber. In this way, each channel has a closed metallic wall which is impenetrable for the electrolyte and at which the detecting reaction can take place completely.

An etching technique is applicable for machining the support body for forming the break through either in steps or in one work step. For this purpose, the support body is made of a material which can be removed by an etching process with the coating however being made of a material which resists the applied etching process. This is advantageously the case if the coating is made of a metal more precious than the support body. The support body is then removed until the coating is exposed and as soon as this occurs, the etching process stops automatically without attacking the coating.

The coating is preferably applied by a galvanic precipitation. With this operation, an especially good adherence of the coating to the support body is obtained and it defines then a good base for the subsequent application of the membrane layer which preferably is applied via a polymerization operation. The polymerization operation establishes an especially intimate connection between the membrane layer and the coating which remains adherent even with subsequent handling of the coated support body.

With the method of the invention for producing the measuring electrode structure, it is possible to utilize many methods for applying the coating and the membrane which all realize the intimate contact of coating and membrane. In addition to the galvanic precipitation, a sputtering operation for generating the coating can be selected. The membrane can either be formed by plasma polymerization or by electro-polymerization. Both polymerization processes provide good adhering layer connections. As further methods for applying the membrane, the immersion film method or sinter film method can be utilized. Likewise, the spin-coating process is suitable which provides good layers in a thickness range of 1 micrometer. Such a membrane layer is also especially stable with respect to form so that larger break throughs with a surface of up to several square centimeters can be obtained without it being necessary to provide an additional support for the exposed membrane.

Because of the number of possible methods which can be used for applying membrane and coating, many more substances can be used for this purpose so that material used and coating methods can be matched advantageously to one another.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
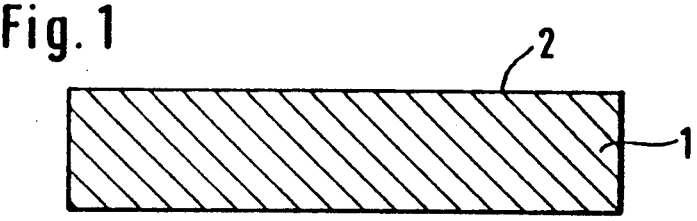
FIGS. 1 to 4 show the method steps for producing a measuring sensor according to the invention.
Figure 2:
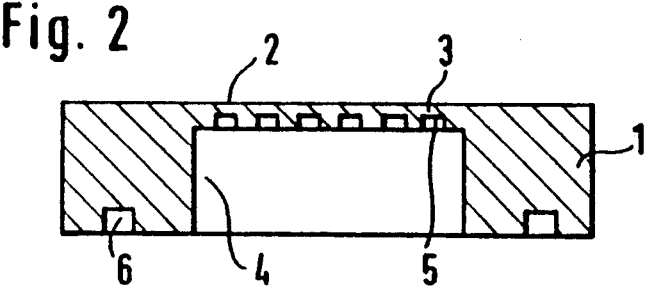

FIG. 1 shows a support body which has not yet been processed. The support body 1 is made of silver, has a thickness of approximately 2 mm and a circular diameter of 20 mm. The front side 2 of support body 1 is polished preparatory to the application of coating 7 and membrane layer 8 shown in FIG. 3. As the next work step, the structures necessary for the later operation are machined into the body from the rear side as shown in FIG. 2. A substantial portion of the support body 1 is removed for the cavity 4 which extends close to the front side 2 with recesses 5 being machined into the supporting layer 3 which still remains. The recesses 5 are provided in preparation for the break throughs which are produced later. Further assembly assists exemplified for example by the circularly-shaped ring slot 6 can likewise be introduced in this manufacturing step.

Figure 3:
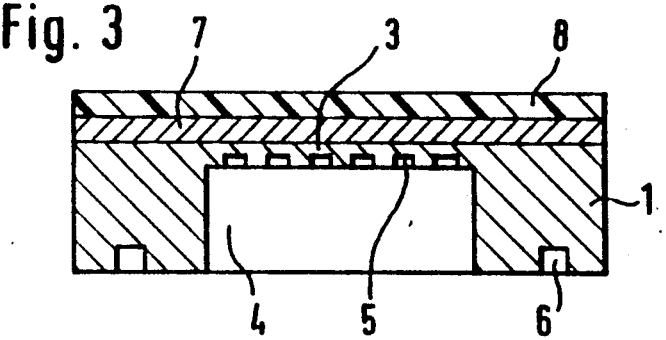

The support body prepared in this manner thereafter receives an electrically-conductive coating 7 as shown in FIG. 3. The coating 7 is applied by sputtering the same onto the front side 2. The coating 7 is made of a metal more precious than the support body 1. For this purpose, metals such as platinum, palladium, iridium or ruthenium can be used. The sputtered coating 7 adheres tightly to the supporting layer 3. A membrane layer 8 is tightly applied to the coating 7 via a polymerization operation. Perfluoropolymer is a suitable polymer for this purpose and is applied as a very thin layer via the operation of a plasma polymerization. A permanent adherence of the membrane 8 to the coating 7 is achieved when this coating is of iridium oxide ($IrO_2$) or ruthenium oxide ($RuO_2$). The support body 1 continues to be processed as shown in FIG. 4 after the coating 7 and the layer 8 have been applied.

The support body 1 is preferably made of titanium or nickel when, for example, iridium oxide ($IrO_2$) or ruthenium oxide ($RuO_2$) are applied. On the other hand, the support body 1 is made of silver when a platinum coating is selected.

Figure 4:
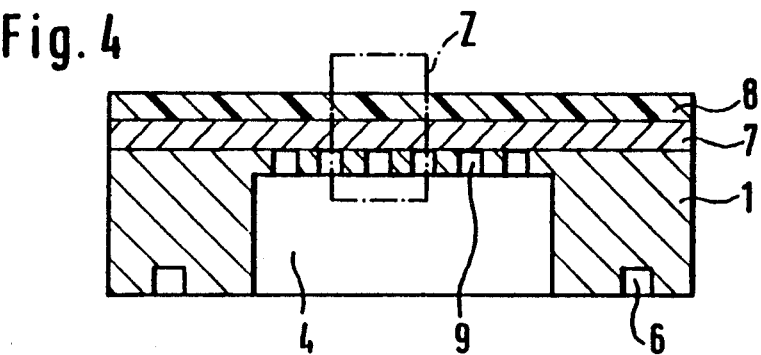
Figure 5:
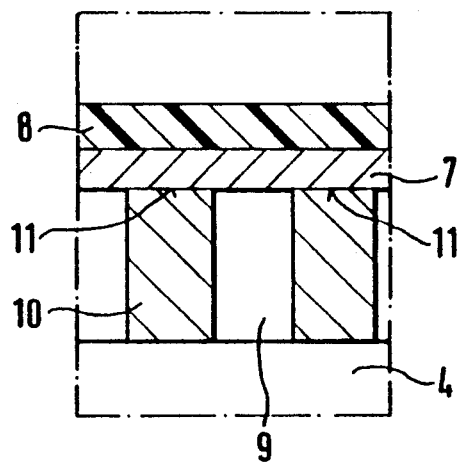
FIG. 5 is an enlarged view of detail Z of FIG. 4 showing a section view of a channel in the support body; and, FIG. 6 shows an embodiment of an assembled measuring sensor according to the invention.

The channels 9 shown in FIGS. 4 and 5 are formed by further removal in the material of the supporting layer 3 from the bottoms of recesses 5 up to the coating 7. The recesses 5 shown in FIG. 3 are thereby deepened to define the channels 9 shown in FIGS. 4 and 5 which extend from the cavity 4 (FIGS. 4 and 5) up to the rear side of the coating 7 (FIGS. 4 and 5). The end face 11 (FIG. 5) of the canal web 10 (FIG. 5) remains as an adhering attachment for the coating 7 on the support body 1 in the region of the cavity 4. The electrolyte is filled into the cavity 4 in a completely assembled measuring sensor shown in FIG. 6. At the end face 11, an impenetrable adherence region is provided into which the electrolyte cannot creep. As shown in the detail Z shown in FIG. 5, the reaction region essential for the electrochemical detection reaction is bounded exclusively by the walls of the channel 9 on the one hand and by the exposed rear side of the electrically-conductive coating 7. By forming the channels 9 with the aid of an etching process, channel depths can be produced having a diameter/length ratio of between 1 and 100 and the electrochemical reaction takes place entirely within the space of the channel 9. In this way, gaseous components to be detected and not being converted at the coating are prevented from diffusing into the electrolyte chamber of the cavity 4 and thus are also available for the detection reaction.

More specifically, the electrically-conductive coating 7 defining the measuring electrode as well as the membrane layer 8 are applied directly to the support body 1 so that the molecules to be detected (which diffuse through the membrane layer) have a short diffusion path and come directly into contact on the rearward side of the membrane layer with the measuring electrode and the electrolyte. In this way, an electrochemical reaction can take place at the electrolyte/measuring-electrode interface.

Figure 6:
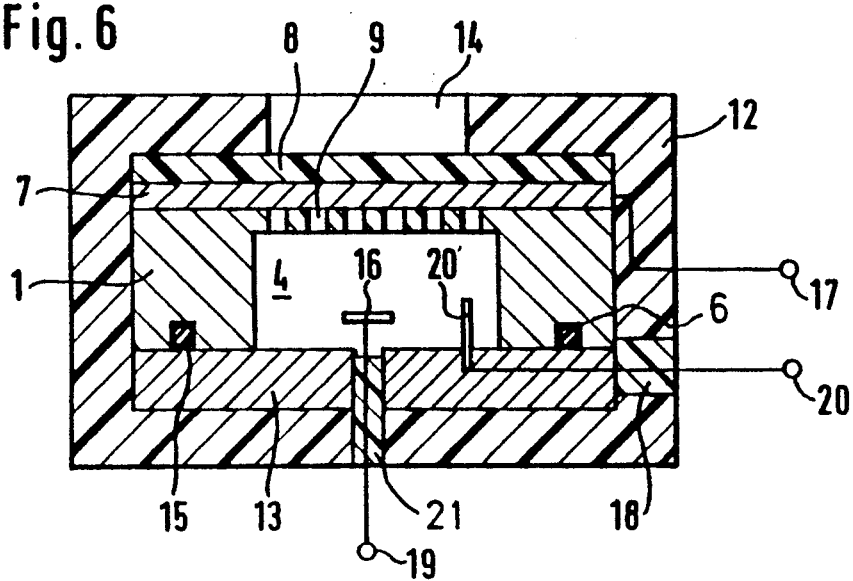

A completely assembled measuring sensor having the support body 1 prepared as described above is shown in FIG. 6. A plastic housing 12 surrounds the support body 1 as well as the membrane layer 8 and a housing base 13. The housing base 13 is sealed with respect to the cavity 4 which defines the electrolyte chamber by means of a ring seal 15 disposed in the ring slot 6. An electrode 20 acts as a reference electrode and is clamped between the housing base 13 and the support body 1 and is passed out of the housing 12 through a lead-through 18. An electric contact 17 is applied to the electrically-conductive coating 7 as shown in FIG. 6. A counter electrode 16 is disposed in the electrolyte chamber 4 and is provided with an electrode terminal 19 passed through a further lead-through 21.

For measuring, the measuring sensor is exposed to a gaseous specimen containing the components to be detected. The specimen penetrates to the membrane layer 8 through the pass-through opening 14 in the housing 12. Only such molecules diffuse through the membrane layer 8 for which this membrane layer is permeable. After the molecules pass through the coating 7, these molecules to be detected react at the boundary surface (electrolyte in channel 9/surface of coating 7/membrane 8) and form reaction products.

An embodiment of the measuring sensor of the invention having a measuring electrode comprising coating 7 made of ruthenium oxide can be advantageously used for making amperometric measurements of oxygen. A measuring sensor of the invention provided with a coating 7 made of iridium oxide can be used to make potentiometric measurements of $CO_2$ and can be generally used as a pH electrode. Basically, the measuring cell having a measuring electrode made either of ruthenium oxide or of iridium oxide can be used to measure oxygen; however, iridium oxide is more expensive.

According to another feature of the invention, the membrane 8 can be a dielectric polymer film formed with the aid of a parylene coating process used in the electronics industry. The chemical characteristics of this film and the process for producing the same are described, for example, in Römpps Chemie-Lexikon, page 2515, published by Franckh'sche Verlagshandlung, Stuttgart (1974). The membrane 8 made in accordance with the parylene coating process has a better permeability for carbon dioxide than for oxygen.

When utilizing an iridium oxide or ruthenium oxide coating 7 on the support body 1, an improved adherence of the parylene is obtained by first applying silane as an adhesive.

The measuring electrode is formed by the coating 7 and the break through or channel 9. At this measuring electrode, an electrical signal is generated which is taken off at signal terminal 17 and electrode terminal 19 and transmitted to a measuring apparatus not shown. The current generated by this measuring reaction is displayed in a calibrated measuring apparatus as a measuring value with the dimension "concentration".

As FIG. 6 shows, no sealing problems for sealing the electrolyte chamber 4 with respect to the ambient are presented by the advantageous configuration provided by measuring sensor. More specifically, the coating 7 and layer 8 on the support body 1 do not require further sealing.

The membrane 8 and the measuring electrode 7 are both applied to the support body as adhering layers and the break through in the supporting body is formed by removing a portion thereof starting from the rearward face and continuing through to the front face. The remaining support body and more particularly its periphery acts simultaneously as a seal and prevents a leakage of the electrolyte to the ambient in a more effective manner than a sealing ring could achieve.

Also, the signal terminal 17 can be built into the housing base 13. Such sealing measures are manageable and offer no special difficulties.

The number and size of the channels 9 are essentially determined by the particular application, that is, they depend upon the gas to be measured. For example, for an oxygen sensor, nine bores or channels 9 would be etched into the thin region above the cavity 4 with each channel having a diameter of 0.5 mm. The bores or channels 9 are uniformly distributed over the thin region over the cavity 4 with this thin region having a thickness, for example, of 100 $\mu$m.

The area of the thin region of the support body 1 occupied by the channels 9 alone would then be approximately 0.75 to 1 $cm^2$ which would be surrounded with a peripheral zone having an area of 1 to 2 $cm^2$ so that a total of 2 to 3 $cm^2$ would be needed for the thin region in this particular example. Other configurations of the bores or channels 9 would require a different area distribution.

It is understood that the foregoing description is that of the preferred embodiments of the invention and that various changes and modifications may be made thereto without departing from the spirit and scope of the invention as defined in the appended claims.

What is claimed is:

1. A measuring sensor for detecting gaseous components in the ambient, the measuring sensor comprising:

a support body having an end face and defining a chamber;

an electrolyte disposed in said chamber;

a permeable, electrically-conductive coating on said end face;

break through means extending from said chamber to said end face for permitting said electrolyte to penetrate to said coating;

said coating being applied to said end face so as to form an adhering interface;

a membrane separating said electrolyte from the ambient containing the gaseous components and being permeable to said gaseous components;

said membrane being impermeable to said electrolyte in a lateral direction between said support body and said coating and being applied to said coating so as to form an adhering connection with said coating;

an electrical signal lead connected to said coating so as to cause said coating to define a measuring electrode and have an electrochemically active surface at said interface; and, a counter electrode disposed in said electrolyte.

2. The measuring sensor of claim 1, said membrane layer being applied to said coating utilizing a polymerization process.

3. The measuring sensor of claim 1, said break through being defined by a plurality of channels.

4. The measuring sensor of claim 1, said break through being an etched break through formed in said support body.

5. The measuring sensor of claim 1, said coating being a galvanically precipitated coating.

6. The measuring sensor of claim 5, said support body being made of a first metal; said coating being made of a second metal; and, said second metal being more precious than said first metal.

7. The measuring sensor of claim 1, wherein said coating is an iridium oxide coating.

8. The measuring sensor of claim 7, wherein said membrane applied to said coating is a dielectric polymer film applied to said coating utilizing a parylene coating process.

9. The measuring sensor of claim 1, wherein said coating is a ruthenium oxide coating.

10. The measuring sensor of claim 9, wherein said membrane applied to said coating is a dielectric polymer film applied to said coating utilizing a parylene coating process.

11. The measuring sensor of claim 1, wherein said coating is made of a sputtered metal selected from the group consisting of iridium, ruthenium, platinum and palladium.

12. The measuring sensor of claim 11, wherein said membrane is a polymer film formed by plasma polymerization.

13. The measuring sensor of claim 11, wherein said membrane is a polymer film formed by electro-polymerization.

14. The measuring sensor of claim 1, wherein said coating is made of a galvanically deposited metal selected from the group consisting of iridium, ruthenium, platinum and palladium.

15. The measuring sensor of claim 14, wherein said membrane is a polymer film formed by plasma polymerization.

16. The measuring sensor of claim 14, wherein said membrane is a polymer film formed by electro-polymerization.

* * * * *